United States Patent [19]

Rizzi

[11] Patent Number: 4,767,743

[45] Date of Patent: Aug. 30, 1988

[54] PEPTIDE IMMUNOSTIMULANTS

[75] Inventor: James P. Rizzi, Waterford, Conn.

[73] Assignee: Pfizer Inc., New York, N.Y.

[21] Appl. No.: 900,934

[22] Filed: Aug. 27, 1986

[51] Int. Cl.$^4$ .................. C07K 5/08; A61K 37/02
[52] U.S. Cl. .................................. 514/18; 530/331;
530/332; 424/88
[58] Field of Search ............... 530/331, 332; 562/509,
562/565; 560/125, 169; 514/18, 19; 424/88

[56] References Cited

U.S. PATENT DOCUMENTS 4,354,966 10/1982 Kitaura et al. ............... 260/112.5 R

OTHER PUBLICATIONS

Chem. Abstr. vol. 93 No. 47159u, 1980 (Okada et al., Abstract of Koenshu-Iyo Masu Kenkyu Kai vol. 3 pp. 249–255 1978).
Chem. Abstr. vol. 87, No. 147351v, 1977 (Okada et al., Abstract of Chem. Pharm. Bull. vol. 25(7), pp. 1497–1508, 1977).
Okada et al., Chem. Pharm. Bull. vol. 25(7) pp. 1497–1508 (1977).

Primary Examiner—Delbert R. Phillips
Assistant Examiner—Christina Chan

Attorney, Agent, or Firm—Peter C. Richardson; Albert E. Frost; James M. McManus

[57] ABSTRACT

Peptide components of formula 1, pharmaceutically acceptable base salts thereof, pharmaceutical compositions and their use as antiinfective agents

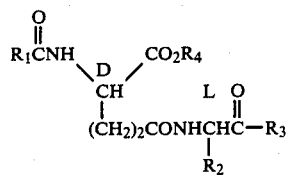

where $R_1$ is alkyl, cycloalkyl or cycloalkylmethyl; $R_2$ is hydrogen or alkyl and $R_3$ is hydroxy or an amino acid residu of the formula

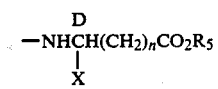

where X is hydrogen, alkyl or hydroxymethyl and n is an integer of 0 to 4 and $R_4$ and $R_5$ are alkyl, hydrogen, benzyl or cyclohexylmethyl.

31 Claims, No Drawings

PEPTIDE IMMUNOSTIMULANTS

BACKGROUND OF THE INVENTION

This invention relates to novel acyl glutamic acid containing peptides useful as immunostimulant and antiinfective agents; to pharmaceutical compositions thereof and to the use thereof in treating infections.

The relatively new field of immunopharmacology, and particularly that segment thereof which deals with immunomodulation, continues to develop at a rapid pace. A variety of naturally occurring compounds has been investigated, including the tetrapeptide tuftsin, known chemically as $N^2$-[1-($N^2$-L-threonyl-L-lysyl)-L-prolyl]L-arginine. Much attention has been directed to synthetic peptidoglycan derivatives, especially those known as muramyl dipeptides. For summaries of the wide range of compounds investigated as immunomodulators, and especially as immunostimulants, attention is directed to Duker et al., Annu. Rep. Med. Chem., 14, 146–167 (1979), Lederer, J. Med. Chem., 23, 819–825 (1980) and to J. Kralovec, Drugs of the Future, 8, 615–638 (1983).

Immunostimulant peptides have been described in a number of patent specifications:

L-Alanyl-alpha-glutaric acid N-acyl dipeptides in German No. 3,024,355, published Jan. 15, 1981;

tetra- and penta-peptides containing D-alanyl-L-glutamyl moieties or L-alanyl-D-glutamyl moieties in British No. 2,053,231, published Feb. 4, 1981 and German No. 3,024,281, published Jan. 8, 1981, respectively; and N-acyl-alanyl-gamma-D-glutamyl tripeptide derivatives in which the C-terminal amino acid is lysine or diaminopimelic acid in German No. 3,024,369, published Jan. 15, 1981; and lactoyl tetrapeptides composed of N-lactylalanyl, glutamyl, diaminopimelyl and carboxymethylamino components in EP No. 11283, published May 23, 1980.

Further immunostimulant polypeptides having the formula (A)

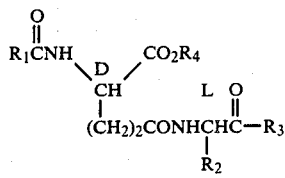

wherein $R^1$ is hydrogen or acyl; $R^2$ is inter alia hydrogen, lower alkyl, hydroxymethyl, benzyl; $R^3$ and $R^4$ are each hydrogen, carboxy, —$CONR^7R^8$ wherein $R^7$ is hydrogen, lower alkyl optionally substituted with hydroxy; and $R^8$ is mono- dicarboxy lower alkyl; $R^5$ is hydrogen or carboxy with the proviso that when one of $R^4$ and $R^5$ is hydrogen, the other is carboxy or —$CONR^7R^8$; $R^6$ is hydrogen; m is 1 to 3 and n is 0 to 2, and derivatives thereof in which the carboxy and amino groups are protected are disclosed in U.S. Pat. Nos. 4,311,640 and 4,322,341; EP applications Nos. 25,482; 50,856; 51,812; 53,388; 55,846 and 57,419.

None of the polypeptides disclosed in the art has a heterocyclyl moiety at the position occupied by variable $R^4$ in the above formula except for U.S. application Ser. No. 662,668, filed Oct. 19, 1984, now U.S. Pat. No. 4,619,915. U.S. application Ser. No. 595,169, filed Mar. 30, 1984, now U.S. Pat. No. 4,565,653 by Ives et al., describes polypeptides wherein variable $R^4$ is a basic amino acid moiety.

Kitaura et al., J. Med. Chem., 25, 335–337 (1982) report $N^2$-(gamma-D-glutamyl)-meso-2(L),2(D)-diaminopimelic acid as the minimal structure capable of eliciting a biological response characteristic of the compound of formula (A) wherein n is 1; $R^1$ is $CH_3CH(OH)$—CO—; $R^2$ is $CH_3$; each of $R^3$ and $R^5$ is —COOH; $R^4$ is —$CONHCH_2COOH$; and $R^6$ is H. Said compound of formula (A) is known as FK-156.

SUMMARY OF THE INVENTION

The novel immunostimulants of the present invention are of the formula

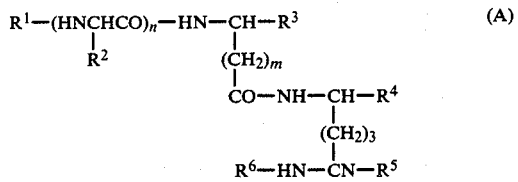

and a pharmaceutically acceptable base salt thereof, wherein $R_1$ is cycloalkyl of four to seven carbon atoms or alkyl of two to ten carbon atoms; $R_2$ is hydrogen or alkyl of one to three carbon atoms; and $R_3$ is hydroxy or an amino acid residue of the formula

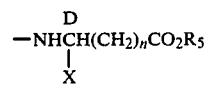

where X is hydrogen, alkyl of one to two carbon atoms or hydroxymethyl and n is an integer of 0 to 4; and $R_4$ and $R_5$ are each hydrogen, alkyl of one to six carbon atoms, cycloalkylmethyl of six to eight carbon atoms or benzyl.

A preferred group of compounds are those where $R_1$ is alkyl of five to eight carbon atoms, $R_2$ is hydrogen, $R_3$ is said amino acid residue where X, n and $R_5$ are as defined, and $R_4$ is hydrogen. Particularly preferred are those compounds within the group where n is 0 and $R_5$ is hydrogen, said alkyl or cyclohexylmethyl. Especially preferred compounds are those wherein $R_1$ is (R,S) 2-ethyl-1-butyl, $R_5$ is hydrogen and X is methyl, $R_1$ is (R,S) 3-heptyl, $R_5$ is hydrogen and X is methyl, $R^1$ is (R,S) 2-methyl-1-pentyl, $R_5$ is hydrogen and X is methyl, $R_1$ is (R,S) 2-heptyl, $R_5$ is hydrogen and X is methyl, $R_1$ is (R,S) 2-ethyl-1-pentyl, $R_5$ is hydrogen and X is methyl, $R_1$ is (R,S) 1-hexyl, $R_5$ is hydrogen and X is methyl, $R_1$ is (R,S) 2-ethyl-1-hexyl, $R_5$ is hydrogen and X is methyl, $R_1$ is (S) or (R,S) 2-methyl-1-hexyl, $R_5$ is hydrogen and X is methyl, $R_1$ is (S) or (R,S) 2-ethyl-1-hexyl, X is methyl and $R_5$ is hydrogen and $R_1$ is 1-hexyl, X is methyl and $R_5$ is hydrogen. Also especially preferred is the compound wherein $R_1$ is 1-hexyl, X is hydrogen and n is 3. Especially preferred esters are those wherein $R_1$ is (R,S) 2-ethyl-1-pentyl, X is methyl and $R_5$ is n-butyl, i-butyl or cyclohexylmethyl, $R_1$ is (S) or (R,S) 2-methyl-1-hexyl, X is methyl and $R_5$ is n-butyl, i-butyl or cyclohexylmethyl and $R_1$ is (S) or (R,S) 2-ethyl-1-hexyl, X is methyl and $R_5$ is n-butyl, i-butyl or cyclohexylmethyl.

A second preferred group of compounds are those wherein $R_1$ is cycloalkyl of four to seven carbon atoms, $R_2$ is hydrogen and $R_3$ is said amino acid residue where n is O, X is alkyl of one to two carbon atoms and $R_4$ and $R_5$ are each hydrogen. Especially preferred within this group is the compound where $R_1$ is cyclohexyl and X is methyl.

A third preferred group of compounds are those wherein $R_1$ is alkyl of five to eight carbon atoms, $R_2$ is hydrogen, $R_3$ is said amino acid residue where X is hydrogen or alkyl of one to two carbon atoms, n is an integer of 0 to 4 and $R_5$ is hydrogen and $R_4$ is alkyl of one to six carbon atoms, cycloalkylmethyl of six to eight carbon atoms or benzyl.

The present invention is also directed to a pharmaceutical composition in unit dosage form comprising a pharmaceutically acceptable carrier and an antiinfective or immunostimulant effective amount of a compound of formula 1 and a method for treating an infection in a human suffering therefrom which comprises administering to said human an antiinfective amount of a compound of formula 1.

By pharmaceutically acceptable base salts of said compounds of formula 1 is meant salts with inorganic or organic bases such as alkali metal and alkaline earth metal hydroxides, ammonia, triethylamine, ethanolamine and dicyclohexylamine.

The configuration of the amino acid moieties which make up the compounds of formula 1 is significant as regards the pharmacological activity of said compounds. The most potent activity is observed in the compounds of formula 1 having the stereochemistry indicated in said formula. In those compounds of formula 1 where $R_2$ and X are other than hydrogen, the preferred stereochemistry at said carbon is indicated as L and D, respectively.

Also considered within the scope of the present invention are compounds of formula 1 where $R_3$ is alkoxy, cycloalkoxy, aralkoxy or alkoxy substituted by one or more of the substituents selected from amino, dialkylamino, hydroxy, alkoxy and halo.

DETAILED DESCRIPTION

The compounds of formula 1 are prepared by any of several methods known to those skilled in the art. The methodology involves the formation of peptide linkages between amino acids which, because of their amino and carboxy groups, and frequently the presence of other reactive groups, necessitate the protection of said groups and/or the activation of such groups, particularly the carboxy group, in order to achieve a certain reaction or to optimize such a reaction.

In general, two routes are employed in the synthesis of the compounds of formula 1. The first procedure utilizes the coupling of the fragment

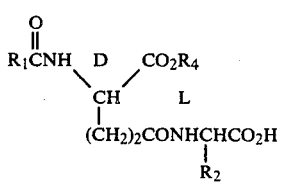

with the amino acid fragment

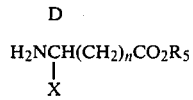

The second procedure comprises acylation of the peptide

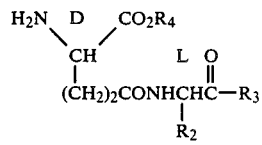

with the appropriate acid $R_1CO_2H$.

In the examples presented herein, certain protecting and activating groups are specifically illustrated. However, one skilled in the art will recognize that other protecting or activating groups could have been used. The choice of a particular protecting group is dependent to a great extent upon the availability of the necessary reagent, its effect upon solubility of the "protected" compound, its ease of removal and the presence of other groups which might be effected by its use; i.e., its selectivity, or its removal.

For example, it will be necessary, or at least desirable, in many reactions to protect the amino groups and/or the carboxy groups. The synthetic route chosen for the peptide synthesis may require removal of one or the other or both of said protecting groups in order to permit further reaction at the regenerated amino or carboxy group; i.e., the protecting groups used are reversible and, in most instances, are removable independently of each other. Additionally, the choice of protecting group for a given amino group depends upon the role of said amino group in the overall reaction scheme. Amino protecting groups having varying levels of lability, i.e., ease of removal, will be used. The same is true as regards carboxy protecting groups. Such groups are known in the art and attention is directed to the reviews by Bodansky et al., "Peptide Synthesis", 2nd Ed., John Wiley & Sons, N.Y. (1976); Greene, "Protective Groups in Organic Synthesis", John Wiley & Sons, N.Y. (1981); McOmie, "Protective Groups in Organic Chemistry", Plenum Press, N.Y. (1973); and to Sheppard in "Comprehensive Organic Chemistry, The Synthesis and Reactions of Organic Compounds", Pergaman Press, N.Y. (1979), edited by E. Haslam, Part 23.6, pages 321-339.

Conventional amino and carboxy protecting groups are known to those skilled in the art. Representative amino protecting groups, but by no means limiting thereof, are the following: such as benzyloxycarbonyl; substituted or unsubstituted aralkyl such as benzyl, trityl, benzhydryl and 4-nitrobenzyl; benzylidene; arylthio such as phenylthio, nitrophenylthio and trichlorophenylthio; phosphoryl derivatives such as dimethylphosphoryl and O,O-dibenzylphosphoryl; trialkylsilyl derivatives such as trimethylsilyl; and others as are described in U.S. Pat. No. 4,322,341 and which are incorporated herein by reference. The preferred amino protecting group is benzyloxycarbonyl. Procedures for substituting said group on a given amino group are well known. In general they comprise acylating the appropriate amino compound with benzyloxycarbonyl chloride (benzylchloroformate) in a reactioninert solvent, e.g., water, methylene chloride, tetrahydrofuran, in the presence of a base (acid acceptor) e.g., sodium or potassium hydroxide when water is solvent; and, when an organic solvent is used, in the presence of a tertiary amine such as $C_{1-4}$ trialkylamines and pyridine. When an aqueous solvent system is used the pH of the reaction is held at about pH 8-10, and preferably at pH 9. Alternatively, when the reactant; i.e., the compound, an amino group of which is to be protected, contains basic groups, it can serve as acid acceptor.

The acyl group, $R_1CO$ is introduced into the peptide by standard acylation procedures as by reacting said peptide with the appropriate acid chloride or bromide in a reaction inert solvent. Favored conditions are non-aqueous conditions including addition of a suitable base such as an organic base, preferably a tertiary amine such as triethylamine, N-methylmorpholine or pyridine. The preferred solvent is methylene chloride.

Representative carboxy protecting groups are various esters such as silyl esters, including trialkyl silyl esters, trihalosilyl esters and haloalkylsilyl esters; certain hydrocarbyl esters such as $C_{1-4}$ alkyl, especially t-butyl groups, benzyl and substituted benzyl esters, benzhydryl and trityl; phenacyl and phthalimidomethyl esters; certain substituted hydrocarbyl esters such as chloromethyl, 2,2,2-trichloroethyl, cyanomethyl; tetrahydropyranyl; methoxymethyl; methylthiomethyl; and others as are described in U.S. Pat. No. 4,322,341 and which are incorporated herein by reference. A highly favored carboxy protecting group is the t-butoxycarbonyl group.

The protected amino and carboxy groups are converted to the unprotected amino and carboxy groups by procedures known to those skilled in the art. The benzyl group, the preferred protecting groups for carboxy (as part of the protected carbazoyl group) groups are removed by catalytic hydrogenation over palladium, especially palladium-on-carbon. Alternatively, said protecting groups are removed by means of trifluoromethanesulfonic acid in trifluoroacetic acid and in the presence of anisole to suppress alkylation. The t-butoxycarbonyl group is readily removed by treatment will dioxane saturated with hydrogen chloride.

Activation of carboxy groups as a menas of expediting a given reaction is methodology known to those skilled in the art. Especially useful in the herein described reaction sequence are the use of anhydrides, particularly cyclic anhydrides; and activated esters, such as those derived from N-hydroxyphthalimide and N-hydroxysuccinimide, both of which are used in peptide syntheses.

The activated N-hydroxysuccinimide esters expedite subsequent reactions at said activated ester groups. As the skilled artisan will recognize other activating groups could be used. A group of particular interest is the N-hydroxyphthalimido group, which group is used in the same manner as is the N-hydroxysuccinimido group. In both instances, a dehydrative coupling agent is used to form the activated ester. Representative of such coupling agents are 1-cyclohexyl-3-(2-morpholinoethyl)-carbodiimide metho-p-toluene sulfonate, dicyclohexyl carbodiimide, N,N'-carbonyldiimidazole, N-(3-dimethylaminopropyl)-N'-ethylcarbodiimide hydrochloride, ethoxyacetylene, diphenylketene and N-ethyl-5-phenylisoxazolene-3'-sulfonate. The reaction conditions for using such coupling agents are well described in the literature. In general they comprise the use of a reactioninert solvent and temperatures ranging from ambient to 100° C. The above-mentioned carbodiimide reagents are favored since they permit use of ambient reaction temperature and afford satisfactory yields of the desired esters.

Upon completion of the coupling reactions leading to the final products, the various protecting groups can be removed by the appropriate techniques previously discussed, and the compounds of formula 1 isolated.

The pharmaceutically acceptable base salts of formula 1 compounds, where $R_3$ is hydroxy or $R_4$ or $R_5$ is hydrogen, are obtained by treating a solution, preferably aqueous solution, thereof with a base such as are enumerated above, generally in stoichiometric proportions. The salts are isolated by evaporation or by precipitation.

The products of this invention are useful as agents in mammals, including humans, for the clinical and therapeutic treatment of diseases caused by various pathogenic microorganisms, especially gram-negative bacteria. They are also useful as immunostimulants in mammals, including humans, having an increased risk of infection due to existing or clinically-induced immunosuppression.

The test procedure, which used $C_3H/HeN$ male mice from the Charles River Breeding Laboratory, is presented below. The mice were acclimatized for 5 days before use and then treated either subcutaneously (SC) or orally (PO) with various dilutions (100, 10, 1 and 0.1 mg/kg) of the test compound or placebo (pyrogen free saline) using a volume of 0.2 ml. The treatment regiment was dependent on the infectious organism utilized: $-24$ and 0 hours before challenge for *Klebsiella pneumoniae* in normal mice; and $-3$, $-2$ and $-1$ day before challenge for *Escherichia coli* or *Staph. aureus* in immunocompromised mice. Challenge was administered intramuscularly (IM) in the hip in the case of *K. pneumoniae* or intraperitoneally (IP) in the case of *E. coli* and *Staph. aureus*. A volume of 0.2 ml. was used for the challenge. Mortality was recorded after 7 days in the case of *K. pneumoniae* and after 3 days in the case of the other two microorganism challenges.

Culture Preparation

*K. pneumoniae, E. coli*, or *Staph. aureus:* the culture was streaked for purity from frozen blood stock on brain heart infusion (BHI) agar. Three colonies were picked from the 18 hour plate culture and placed into 9 ml. of BHI broth. The broth culture was grown for 2 hours at 37° C. on a rotary shaker after which 0.2 ml. was streaked on the surface of several BHI agar slants. Following an 18 hour incubation at 37° C., the slants were washed with BHI broth, the culture density adjusted using a spectronic 20 and the appropriate dilution made to achieve an LD90 challenge level in normal mice.

When used as antiinfective or immunostimulant agents in humans, the compounds of this invention are conveniently administered via the oral, subcutaneous, intramuscular, intravenous or intraperitoneal routes, generally in composition form. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 50 to about 500 mg. are suitable for most applications.

The physician will determine the dosage which will be most suitable for an individual patient and it will vary with the age, weight and response of the particular patient and the route of administration. The favored oral dosage range, in single or divided doses, is from about 1.0 to about 300 mg/kg/day. The favored parenteral dose is from about 1.0 to about 100 mg/kg/day; the preferred range from about 1.0 to about 20 mg/kg/day.

This invention also provided pharmaceutical compositions, including unit dosage forms, valuable for the use of the herein described compounds for the utilities disclosed herein. The dosage form can be given in single or multiple doses, as previously noted, to achieve the daily dosage effective for a particular utility.

The following examples are provided solely for the purpose of further illustration. In the interest of brevity, the following abbreviations for peak shapes in the NMR spectra are used: s, singlet; d, doublet; t, triplet; q, quartet; m, multiplet. The terms mole and millimole are abbreviated as m and mm, respectively.

EXAMPLE 1

N—Heptanoyl-D-gamma-glutamyl—glycyl—D-alanine

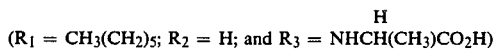

($R_1$ = $CH_3(CH_2)_5$; $R_2$ = H; and $R_3$ = NHCH($CH_3$)$CO_2H$)

1A. N-heptanoyl-D-gamma-glutamyl(alpha benzyl ester)-glycine

To a solution of 897 mg. (13.0 mm) of glycine and 1.3 g. (13.0 mm) of triethylamine in 10 ml. of water was added 5.0 g. (11.2 mm) of N-heptanoyl-D-gamma-glutamyl (alpha benzyl ester)-hydroxysuccinimide ester in 100 ml. of dioxane, and the resulting reaction mixture allowed to stir at room temperature for 80 hours. The solution was poured into 300 ml. of ethyl acetate and the separated organic phase washed with 10% hydrochloric acid, water and a brine solution. The organic phase was separated, dried over magnesium sulfate and concentrated in vacuo to dryness. The residue was triturated with diethyl ether and filtered under nitrogen, 3.43 g. (74% yield).

1B. N-heptanoyl-D-gamma-glutamyl-glycyl-D-alanine

To a solution of 2.0 g. (4.78 mm) of N-heptanoyl-D-gamma-glutamyl(alpha benzyl ester)-glycine, 1.75 g. (5 mm) of D-alanine benzyl ester p-toluenesulfonic acid salt, 506 mg. (5 mm) of triethylamine and 675 mg. (5 mm) of 1-hydroxybenzotriazole in 100 ml. of tetrahydrofuran was added 3.03 g. (7.17 mm) of 1-cyclohexyl-3-(2-morpholinoethyl)carbodiimide metho-p-toluenesulfonate and the reaction mixture stirred at room temperature for 18 hours. The reaction mixture was poured into 300 ml. of ethyl acetate and the organic phase separated and washed with 10% hydrochloric acid, water, a saturated sodium bicarbonate solution and a brine solution. The organic phase was separated, dried over magnesium sulfate and concentrated in vacuo. The residue was triturated with diethyl ether and filtered under nitrogen, 2.7 g. Two grams of the solid in 75 ml. of methanol with 400 mg. of 10% palladium hydroxide on charcoal was shaken in a hydrogen atmosphere at an initial pressure of 50 psi for 4 hours. The catalyst was filtered and the filtrate evaporated under reduced pressure and the residue was dissolved in water and lyophilized to give 1.23 g. (90% yield) of the desired product as a white solid.

The NMR spectrum (DMSO-$d_6$) showed absorption at 4.35–4.2 (m, 2H), 3.83 (s, 2H), 2.35 (t, J=7Hz, 2H), 2.17 (t, J=7Hz, 2H), 2.1–1.8 (m, 2H), 1.55–1.45 (m, 2H), 1.3 (d, J=6Hz, 3H), 1.17 (bs, 6H) and 0.75 (bs, 3H) ppm.

EXAMPLE 2

N-Heptanoyl-D-gamma-glutamyl-glycine ($R_1$=$CH_3(CH_2)_5$; $R_2$=H; and $R_3$=OH)

A solution containing 1.0 g. of N-heptanoyl-D-gamma-glutamyl (alpha benzyl ester)-glycine in 50 ml. of methanol was treated with 100 mg. of 10% palladium hydroxide on charcoal and shaken in a hydrogen atmosphere at 50 psi for 3 hours. The catalyst was filtered and the filtrate concentrated in vacuo. The residue was dissolved in hot water and evaporated in vacuo. The residue was redissolved in water and lyophilized to give 630 mg. (83% yield) of the desired product as a white solid.

The NMR spectrum (DMSO-$d_6$) showed absorption at 4.37–4.25 (m, 1H), 3.9 (s, 2H), 2.35 (t, J=7Hz, 2H), 2.18 (t, J=6Hz, 2H), 2.4–1.8 (m, 2H), 1.6–1.4 (m, 2H), 1.8 (bs, 6H) and 0.7 (bt, 3H) ppm.

EXAMPLE 3

N-Heptanoyl-D-gamma-glutamyl-glycyl-glycine ($R_1$=$CH_3(CH_2)_5$; $R_2$=H; and $R_3$=NHCH$_2$CO$_2$H

3A. N-heptanoyl-D-gamma-glutamyl; (alpha benzyl ester)glycine hydroxysuccinimide ester To a cold solution (0° C.) of 13.0 g. (31 mm) of N-heptanoyl-D-gamma-glutamyl (alpha benzyl ester)glycine and 3.91 g. (34 mm) of N-hydroxysuccinimide in 400 ml. of tetrahydrofuran was added 7.0 g. (34 mm) of dicyclohexylcarbodiimide, and the mixture allowed to stir at 0° C. for one hour and at room temperature for 18 hours. The solids were filtered and the filtrate concentrated under reduced pressure. The residue was triturated with diethyl ether and filtered under nitrogen to give 15.4 g. (98%) of the desired intermediate.

3B. N-heptanoyl-D-gamma-glutamyl-glycyl-glycine

To 2.0 g. (3.97 mm) of N-heptanoyl-D-gamma-glutamyl (alpha benzyl ester)-glycine hydroxysuccinimide ester in 100 ml. of dioxane was added 446 mg. (5.95 mm) of glycine and 0.55 ml. (3.9 mm) of triethylamine in 10 ml. of water, and the resulting reaction mixture allowed to stir at room temperature for 18 hours. The solution was poured into 100 ml. of ethyl acetate and the organic layer washed with 2.5% hydrochloric acid, water and a brine solution. The organic layer was separated, dried over magnesium sulfate and concentrated to dryness. The residue was triturated with diethyl ether and filtered under nitrogen to give 1.7 g. of white solid. One and five-tenths grams of the solid in 75 ml. of methanol containing 200 mg. of 10% palladium hydroxide on carbon was shaken in a hydrogen atmosphere at 50 psi for 3 hours. The catalyst was filtered and the filtrate concentrated in vacuo. The residue was dissolved in water and lyophilized to give 1.12 g. (90% yield) of the desired product.

The NMR spectrum (DMSO-$d_6$) showed absorption at 8.2–8.0 (m, 3H), 4.19 (m, 1H), 4.8–4.6 (m, 4H), 2.25 (t, J=7Hz, 2H), 2.1 (t, J=6Hz, 2H), 2.05–1.7 (m, 2H), 1.5 (m, 2H), 1.25 (bs, 6H) and 0.85 (t, J=6Hz, 3H) ppm.

EXAMPLE 4

N—Heptanoyl-D-gamma-glutamyl—glycyl—D-serine

$(R_1 = CH_3(CH_2)_5; R_2 = H; \text{ and } R_3 = -NHCH(CH_2OH)CO_2H)$

Starting with 2.0 g. (3.98 mm) of N-heptanoyl-D-gamma-glutamyl (alpha benzyl ester)-glycine hydroxysuccinimide ester, 780 mg. (4.02 mm) of O-benzyl-D-serine and 0.556 ml. (4.02 mm) of triethylamine and following the procedure of Example 3B, 902 mg. (76% yield) of the desired product is isolated, m.p. 130°–132° C.

The NMR spectrum (DMSO-$d_6$) showed absorption at 8.36–7.94 (m, 3H), 4.46–4.28 (m, 1H), 4.28–4.08 (m, 1H), 3.94–3.50 (m, 4H), 2.25 (t, J=9Hz, 2H), 2.17 (t, J=9Hz, 1H), 2.10–1.04 (m, 14H) and 0.9 (t, J=6Hz, 3H) ppm.

EXAMPLE 5

N-Heptanoyl-D-gamma-glutamyl-glycyl-D-alpha-aminobutyric acid ($R_{1D}=CH_3(CH_2)_5$—; $R_2$=H; and $R_3$=—NHCH(CH$_2$CH$_3$)CO$_2$H)

The procedure of Example 3B was repeated, starting with 2.0 g. (3.98 mm) of N-heptanoyl-D-gamma-glutamyl (alpha benzyl ester)-glycyl hydroxysuccinimide ester, 400 mg. (4.02 mm) of D-alpha-aminobutyric acid and 0.556 ml. (4.02 mm) of triethylamine, to give 632 mg. (57% yield) of the desired product, m.p. 140°–141° C.

The NMR spectrum (DMSO-$d_6$) showed absorption at 8.16–8.04 (m, 3H), 4.22–4.08 (m, 2H), 3.84–3.58 (m, 2H), 2.2 (t, J=9Hz, 2H), 2.12 (t, J=9Hz, 2H), 2.04–1.0 (m, 15H) and 0.85 (t, J=6Hz, 6H) ppm.

EXAMPLE 6

N-Heptanoyl-D-gamma-glutamyl-glycyl-3-aminopropionic acid ($R_1$=CH$_3$(CH$_2$)$_5$—; $R_2$=H; and $R_3$=—NH(CH$_2$)$_2$CO$_2$H)

Following the procedure of Example 3B and starting with 1.5 g. (3.0 mm) of N-heptanoyl-D-gamma-glutamyl (alpha benzyl ester)-glycine hydroxysuccinimide ester, 350 mg. (3.9 mm) of 3-aminopropionic acid and 0.55 ml. (3.9 mm) of triethylamine, 500 mg. (43% yield) of the desired product was obtained, m.p. 135°–138° C.

The NMR spectrum (DMSO-$d_6$) showed absorption at 8.19–8.02 (m, 2H), 7.98–7.87 (t, J=5Hz, 1H), 4.25–4.1 (m, 2H), 3.8–3.49 (m, 2H), 3.44–3.1 (m, 2H), 2.4 (t, J=6Hz, 2H), 2.22 (t, J=7Hz, 2H), 2.14 (t, J=7Hz, 2H), 2.1–1.67 (m, 2H), 1.6–1.17 (m, 8H) and 0.88 (t, J=6Hz, 3H) ppm.

EXAMPLE 7

N-Heptanoyl-D-gamma-glutamyl-glycyl-4-aminobutyric acid ($R_1$=CH$_3$(CH$_2$)$_5$—; $R_2$=H; and $R_3$=—NH(CH$_2$)$_3$CO$_2$H)

The procedure of Example 6 was repeated substituting 410 mg. (4.0 mm) of 4-aminobutyric acid for the 3-aminopropionic acid to give 600 mg. (50% yield) of the desired product, m.p. 140°–142° C.

The NMR spectrum (DMSO-$d_6$) showed absorption at 8.18–8.03 (m, 2H), 7.88 (bt, J=4Hz, 1H), 4.17–4.09 (m, 2H), 3.81–3.48 (m, 2H), 2.32–2.08 (m, 6H), 2.08–1.08 (m, 12H) and 0.88 (t, J=6Hz, 3H) ppm.

EXAMPLE 8

N-Heptanoyl-D-gamma-glutamyl-glycyl-5-aminopentanoic acid ($R_1$=CH$_3$(CH$_2$)$_5$—; $R_2$=H; and $R_3$=—NH(CH$_2$)$_4$CO$_2$H)

Substituting 470 mg. (4.0 mm) of 5-aminopentanoic acid for 3-aminobutyric acid and following the procedure of Example 6, 520 mg. (42% yield) of the desired product was obtained, m.p. 122°–124° C.

The NMR spectrum (DMSO-$d_6$) showed absorption at 8.25–7.94 (m, 2H), 7.85 (t, J=5Hz, 1H), 4.25–4.1 (m, 2H), 3.82–3.46 (m, 2H), 3.24–2.9 (m, 2H), 2.21–2.08 (m, 6H), 2.08–1.2 (m, 14H) and 0.88 (t, J=6Hz, 3H) ppm.

EXAMPLE 9

N-Heptanoyl-D-gamma-glutamyl-glycyl-6-aminohexanoic acid ($R_1$=CH$_3$(CH$_2$)$_5$—; $R_2$=H; and $R_3$=—NH(CH$_2$)$_5$CO$_2$H)

The procedure of Example 6 was again repeated, substituting 530 mg. (4.0 mm) of 6-aminohexanoic acid for the 3-aminobutyric acid to give 520 mg. (40% yield) of the desired product as a white foam.

The NMR spectrum (DMSO-$d_6$) showed absorption at 8.28–7.9 (m, 2H), 7.82 (bt, J=4Hz, 1H), 4.27–4.1 (m, 2H), 3.81–3.47 (m, 2H), 3.15–2.90 (m, 2H), 2.3–2.08 (m, 6H), 2.08–1.18 (m, 16H) and 0.88 (t, J=6Hz, 3H) ppm.

EXAMPLE 10

N—Isovaleryl-D-gamma-glutamyl—glycyl—D-alanine

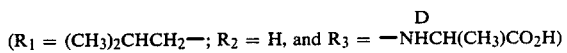

$(R_1 = (CH_3)_2CHCH_2—; R_2 = H, \text{ and } R_3 = -NHCH(CH_3)CO_2H)$

10A. glycyl-D-alanine benzyl ester hydrochloride

To a cold (0° C.) solution of 100 ml. methylene chloride containing 10 g. (57 mm) of N-t-butyloxycarbonylglycine, 20 g. (57 mm) of D-alanine benzyl ester p-toluenesulfonic acid salt and 5.77 g. (57 mm) of triethylamine was added 12.3 g. (60 mm) of dicyclohexylcarbodiimide and the resulting reaction mixture allowed to warm to room temperature. After 18 hours the mixture was filtered and the filtrate concentrated in vacuo. The residue was dissolved in 200 ml. of ethyl acetate and the organic layer washed with 2.5% hydrochloric acid, water, a saturated sodium bicarbonate solution and a brine solution. The organic layer was separated, dried over magnesium sulfate and evaporated under reduced pressure. To the resulting oil 200 ml. of dioxane saturated with hydrogen chloride was added. After 30 minutes 400 ml. of diethyl ether was added and the product filtered under nitrogen, 10.9 g. (70% yield).

10B. N-t-butoxycarbonyl-D-gamma-glutamyl (alpha benzyl ester) hydroxysuccinimide ester To 1500 ml. of methylene chloride containing 50 g. (143 mm) of N-t-butoxycarbonyl-D-gamma glutamic acid alpha-benzyl ester and 17.3 g. (150 mm) of N-hydroxysuccinimide was added 30.9 g. (15 mm) of dicyclohexylcarbodiimide and the resulting reaction mixture allowed to stir at room temperature for 18 hours. The solids were filtered and the filtrate concentrated in vacuo. The residue was triturated with diethyl ether and the solids filtered under nitrogen, 43.7 g. (68% yield).

10C. D-gamma-glutamyl (alpha benzyl ester)-glycyl-D-alanine benzyl ester hydrochloride A solution containing 4.3 g. (9.45 mm) of N-t-butoxycarbonyl-D-gamma-glutamyl (alpha benzyl ester) hydroxysucinimide ester, 2.71 g. (9.92 mm) of glycyl-D-alanine benzyl ester hydrochloride and 1.0 g. (9.92 mm) of triethylamine in 100 ml. of methylene chloride was allowed to stir at room temperature for 18 hours, and was then concentrated in vacuo. The residue was dissolved in 200 ml. of ethyl acetate and the solution washed with 2.5% hydrochloric acid, water, 10% potassium carbonate and a brine solution. The organic phase was separated, dried over magnesium sulfate and evaporated under reduced pressure. The residue was treated with 200 ml. of dioxane saturated with hydrogen chloride and allowed to stir for 2 hours. The solution was concentrated to dryness in vacuo and the residue triturated with diethyl ether. The solids were filtered under nitrogen, 3.41 g. (73% yield).

10D. N-isovaleryl-D-gamma-glutamyl-glycyl-D-alanine

To a solution of 1.0 g. (2.03 mm) of D-gamma-glutamyl (alpha benzyl ester)-glycyl-D-alanine benzyl ester hydrochloride and 616 mg. (6.09 mm) of triethylamine in 50 ml. of methylene chloride was added 490 mg. (4.06 mm) of iso-valeryl chloride and the reaction mixture stirred at room temperature for 80 hours. The methylene chloride was evaporated in vacuo and the residue dissolved in ethyl acetate. The resulting solution was washed with 2.5% hydrochloric acid, water 10% potassium carbonate, water, and a brine solution. The organic phase was separated, dried over magnesium sulfate and concentrated under vacuum. The residue was triturated with diethyl ether, filtered under nitrogen (910 mg.) and 700 mg. dissolved in 50 ml. of methanol. Palladium hydroxide 200 mg. was added to the solution and the mixture shaken in a hydrogen atmosphere at 50 psi for 3 hours. The catalyst was filtered and the solvent removed in vacuo. The residue was dissolved in water and lyophilized to give 364 mg. (65% yield) of the desired product.

The NMR spectrum (DMSO-$d_6$) showed absorption at 8.25-8.05 (m, 3H), 4.33-4.12 (m, 2H), 3.72 (d, J=6Hz, 2H), 2,21 (t, J=8Hz, 2H), 1.88-1.68 (m, 1H), 2.08-1.9 (m, 4H), 1.28 (d, J=9Hz, 3H) and 0.9 (d, J=7Hz, 6H) ppm.

EXAMPLE 11

Starting with the appropriate acid chloride and D-gamma-glutamyl (alpha benzyl ester)-glycyl-D-alanine benzyl ester hydrochloride and employing the procedure of Example 10D, the following compounds were prepared:

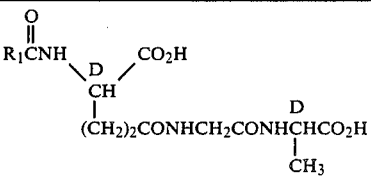

| $R_1$ | m.p., °C. | NMR, ppm |
|---|---|---|
| $CH_3(CH_2)_8-$ | >175 | (DMSO-$d_6$) 8.17-8.22 (m, 2H), 4.35-4.13 (m, 2H), 3.83 (d, J=6Hz, 2H), 2.22 (t, J=6Hz, 2H), 2.15 (t, J=6Hz, 2H), 2.08-1.65 (m, 2H), 1.45-1.18 (m, 17H) and 0.90 (t, J=7Hz, 3H) |
| $(CH_3)_2CH-$ | >110 (dec) | (DMSO-$d_6$) 8.2-8.08 (m, 2H), 8.02 (d, J=9Hz, 1H), 4.3-4.1 (m, 2H), 3.72 (d, J=7Hz, 2H), 2.53-2.40 (m, 1H), 2.22 (t, J=9Hz, 2H), 2.10-1.7 (m, 2H), 1.28 (d, J=9Hz, 3H) and 1.08-0.9 (m, 6H) |
| ⌬(s) | >110 (dec) | (DMSO-$d_6$) 8.3-7.9 (m, 3H), 4.33-4.17 (m, 2H), 3.72 (d, J=5Hz, 2H), 2.3-2.1 (m, 2H) and 2.10-1.0 (m, 16H) |
| $CH_3(CH_2)_2-$ | >110 (dec) | (DMSO-$d_6$) 8.25-8.05 (m, 3H), 4.35-4.22 (m, 2H), 3.72 (d, J=6Hz, 2H), 2.22 (t, J=8Hz, 2H), 2.12 (t, J=8Hz, 2H), 2.08-1.77 (m, 2H), 1.55 (q, J=8Hz, 2H), 1.28 (d, J=8Hz, 3H) and 0.88 (t, J=7Hz, 3H) |
| $CH_3(CH_2)_4-$ | >190 (dec) | (DMSO-$d_6$) 8.33-8.0 (m, 3H), 4.35-4.1 (m, 2H), 3.7 (d, J=6Hz, 2H), 2.17 (t, J=8Hz, 2H), 2.1 (t, J=8Hz, 2H), 2.05-1.63 (m, 2H), 1.48 (t, J=7Hz, 2H), 1.2-1.1 (m, 7H) and 0.85 (t, J=7Hz, 3H) |
| $CH_3(CH_2)_6-$ | >180 (dec) | ($D_2O$) 4.42-4.28 (m, 2H), 3.91 (s, 1H), 2.4 (t, J=7Hz, 2H), 2.27 (t, J=7Hz, 2H), 2.22-1.94 (m, 2H), 1.65-1.55 (m, 2H), 1.39 (d, J=8Hz, 3H), 1.34-1.17 (m, 8H) and 0.73 (m, 3H) |
| $CH_3(CH_2)_3\overset{\underset{\displaystyle CH_3}{\mid}}{CH}CH_2-$ (s) | — | (DMSO-$d_6$) 8.27-8.03 (m, 3H), 4.32-4.1 (m, 2H), 3.72 (d, J=6Hz, 2H), 2.22 (t, J=10Hz, 2H), 2.27-1.68 (m, 6H), 1.42-1.0 (m, 10H) and 0.94-0.8 (m, 6H) |
| $CH_3(CH_2)_3\overset{\underset{\displaystyle CH_2CH_3}{\mid}}{CH}-$ (R,S) | — | (DMSO-$d_6$) 8.22-8.0 (m, 3H), 4.32-4.1 (m, 2H), 3.8-3.6 (m, 2H), 2.28-1.68 (m, 6H), 1.6-1.0 (m, 12H) and 0.94-0.7 (m, 6H). |

-continued $$R_1CNH-CH(CO_2H)-(CH_2)_2CONHCH_2CONHCH(CH_3)CO_2H$$

| $R_1$ | m.p., °C. | NMR, ppm |
|---|---|---|
| (CH₃CH₂)₂CH— | — | (DMSO—d₆) 8.29–7.97 (m, 3H), 4.33–4.1 (m, 2H), 3.81–3.59 (m, 2H), 2.32–1.65 (m, 6H), 1.65–1.17 (m, 8H) and 1.02–0.68 (m, 6H) |
| (s)-cyclohexyl-CH₂— | — | (DMSO—d₆) 8.3–8.0 (m, 3H), 4.32–4.1 (m, 2H), 3.85–3.62 (m, 2H), 2.21 (t, J=8Hz, 2H), 2.02 (d, J=8Hz, 2H), 2.01–1.9 (m, 1H), 1.85–1.5 (m, 8H), 1.28 (d, J=8Hz, 3H) and 1.28–0.8 (m, 5H) |
| (CH₃CH₂CH₂)₂CHCH₂— | — | (DMSO—d₆) 8.18–8.0 (m, 3H), 4.31–4.1 (m, 2H), 3.84–3.6 (m, 2H), 2.22 (t, J=6Hz, 2H), 2.07 (d, J=8Hz, 2H), 2.03–1.7 (m, 3H), 1.4–1.15 (m, 11H) and 0.87 (t, J=6Hz, 6H) |
| (CH₃CH₂)₂CHCH₂— | — | (DMSO—d₆) 8.27–7.95 (m, 3H), 4.3–4.1 (m, 2H), 3.78–3.6 (m, 2H), 2.3–1.57 (m, 8H), 1.46–1.13 (m, 8H) and 0.84 (t, J=8Hz, 6H) |
| CH₃(CH₂)₃CH(CH₃)CH₂— (R,S) | — | (DMSO—d₆) 8.18–8.0 (m, 3H), 4.24–4.06 (m, 2H), 3.74–3.56 (m, 2H), 2.17 (t, J=9Hz, 2H), 2.12–2.0 (m, 1H), 2.0–1.64 (m, 4H), 1.24 (d, J=6Hz, 7H), 1.14–0.98 (m, 2H) and 0.81 (d, J=6Hz, 6H) |
| CH₃(CH₂)₂CH(CH₃)CH₂— (R,S) | — | (DMSO—d₆) 8.2–8.04 (m, 3H), 4.26–4.08 (m, 2H), 3.76–3.6 (m, 2H), 2.28–1.64 (m, 7H), 1.4–0.96 (m, 7H) and 0.96–0.74 (m, 6H). |
| (CH₃)₂CH(CH₂)₃— | — | (DMSO—d₆) 8.24–7.95 (m, 3H), 4.3–4.08 (m, 2H), 3.81–3.59 (m, 2H), 2.21 (t, J=6Hz, 2H), 2.11 (t, J=8Hz, 2H), 2.05–1.38 (m, 7H), 1.27 (d, J=8Hz, 3H), 1.17–1.05 (m, 2H) and 0.86 (d, J=10Hz, 6H) |

-continued $$R_1CNH-CH(CO_2H)-(CH_2)_2CONHCH_2CONHCH(CH_3)CO_2H$$

| $R_1$ | m.p., °C. | NMR, ppm |
|---|---|---|
| CH₃(CH₂)₄CH(CH₃)— (R,S) | — | (DMSO—d₆) 8.24–8.0 (m, 3H), 4.33–4.11 (m, 2H), 3.79–3.6 (m, 2H), 2.41–2.29 (m, 1H), 2.22 (t, J=8Hz, 2H), 2.11–1.66 (m, 2H), 1.59–1.43 (m, 1H), 1.38–1.11 (m, 11H), 1.06–0.95 (m, 3H) and 0.87 (t, J=6Hz, 3H) |
| CH₃(CH₂)₃CH(CH₂CH₃)CH₂— (R,S) | — | (DMSO—d₆) 8.24–8.02 (m, 3H), 4.32–4.11 (m, 2H), 3.84–3.6 (m, 2H), 2.24 (t, J=8Hz, 2H), 2.08 (d, J=8Hz, 2H), 2.03–1.63 (m, 4H), 1.44–1.11 (m, 12H) and 0.97–0.71 (m, 6H) |
| (CH₃)₂CH(CH₂)₄— | — | (DMSO—d₆) 8.24–8.04 (m, 3H), 4.28–4.1 (m, 2H), 3.76–3.6 (m, 2H), 2.18 (t, J=6Hz, 2H), 2.1 (t, J=6Hz, 2H), 2.04–1.86 (m, 1H), 1.84–1.66 (m, 1H), 1.56–1.38 (m, 3H), 1.23 (d, J=6Hz, 3H), 1.2–1.06 (m, 3H) and 0.82 (d, J=6Hz, 6H) |
| CH₃(CH₂)₄CH(CH₃)CH₂— (R,S) | — | (DMSO—d₆) 8.23–7.98 (m, 3H), 4.3–4.13 (m, 2H), 3.81–3.61 (m, 2H), 2.22 (t, J=8Hz, 2H), 2.18–1.68 (m, 6H), 1.45–1.07 (m, 12H) and 0.98–0.8 (m, 6H) |
| (CH₃)₂CH(CH₂)₂CH(CH₃)CH₂— (R,S) | — | (DMSO—d₆) 8.37–8.03 (m, 3H), 4.31–4.1 (m, 2H), 3.78–3.6 (m, 2H), 2.26 (t, J=8Hz, 2H), 2.2–1.36 (m, 7H), 1.3 (d, J=8Hz, 5H), 1.26–1.05 (m, 2H) and 1.05–0.73 (m, 9H) |
| (CH₃)₂CHCH₂CH(CH₃)CH₂— | — | (DMSO—d₆) 8.23–7.98 (m, 3H), 4.3–4.13 (m, 2H), 3.81–3.61 (m, 2H), 2.21 (t, J=8Hz, 2H), 2.15–2.0 (m, 2H), 1.9 (t, J=8Hz, 2H), 1.85–1.52 (m, 3H), 1.4–1.22 (m, 3H), 1.22–0.94 (m, 3H) and 0.94–0.80 (m, 6H) |

-continued

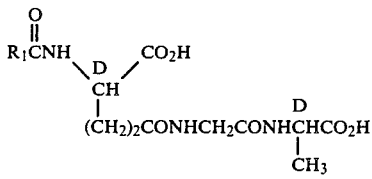

| $R_1$ | m.p., °C. | NMR, ppm |
|---|---|---|
| CH₃CH₂<br>\|<br>CH₃(CH₂)₂CHCH₂—<br>(R,S) | — | (DMSO—d₆) 8.25–7.98 (m, 3H), 4.3–4.08 (m, 2H), 3.81–3.62 (m, 2H), 2.22 (t, J=8Hz, 2H), 2.06 (d, J=8Hz, 2H), 2.02–1.89 (m, 1H), 1.87–1.65 (m, 2H), 1.41–1.06 (m, 11H) and 0.98–0.7 (m, 6H) |
| ⬠—CH₂— | — | (DMSO—d₆) 8.33–7.95 (m, 3H), 4.3–4.06 (m, 2H), 3.83–3.59 (m, 2H), 2.21 (t, J=8Hz, 2H), 2.11 (s, 3H), 2.08–1.87 (m, 1H), 1.87–1.35 (m, 8H), 1.25 (d, J=8Hz, 3H) and 1.22–0.98 (m, 3H) |
| (CH₃CH₂)₂CH(CH₂)₂— | — | (DMSO—d₆) 8.21–8.0 (m, 3H), 4.32–4.1 (m, 2H), 3.83–3.6 (m, 2H), 2.21 (t, J=8Hz, 2H), 2.11 (t, J=8Hz, 2H), 2.05–1.89 (m, 1H), 1.87–1.67 (m, 1H), 1.57–1.38 (m, 3H), 1.38–1.08 (m, 9H) and 0.83 (t, J=6Hz, 6H) |
| CH₃<br>\|<br>CH₃(CH₂)₂CH(CH₂)₂—<br>(R,S) | — | (DMSO—d₆) 8.24–7.97 (m, 3H), 4.33–4.1 (m, 2H), 3.86–3.59 (m, 2H), 2.35–2.08 (m, 4H), 2.08–1.9 (m, 1H), 1.89–1.67 (m, 1H), 1.63–1.46 (m, 1H), 1.46–1.02 (m, 11H) and 0.98–0.73 (m, 6H) |
| CH₃CH₂<br>\|<br>CH₃(CH₂)₄CHCH₂—<br>(R,S) | — | (DMSO—d₆) 8.2–7.94 (m, 3H), 4.26–4.06 (m, 2H), 3.76–3.56 (m, 2H), 2.16 (t, J=6Hz, 2H), 2.1–1.84 (m, 3H), 1.84–1.6 (m, 2H), 1.24 (d, J=6Hz, 9H), 1.12–0.92 (m, 3H) and 0.92–0.64 (m, 9H) |
| CH₃<br>\|<br>CH₃(CH₂)₅CHCH₂—<br>(R,S) | — | (DMSO—d₆) 8.23–8.0 (m, 3H), 4.32–4.06 (m, 2H), 3.72 (d, J=8Hz, 2H), 2.22 (t, J=10Hz, 2H), 2.16–1.7 (m, 6H), 1.42–1.08 (m, 14H) and 0.92–7.0 (m, 6H) |

-continued

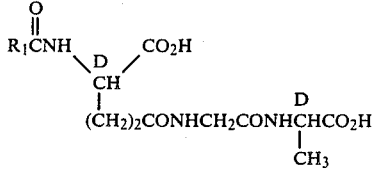

| $R_1$ | m.p., °C. | NMR, ppm |
|---|---|---|
| C₂H₅<br>\|<br>CH₃(CH₂)₃CHCH₂—<br>(S) | — | (DMSO—d₆) 8.2–8.0 (m, 3H), 4.24–4.16 (m, 2H), 3.74–3.60 (m, 2H), 2.18 (t, J=7, 2H), 2.02 (d, J=7, 2H), 2.02–1.6 (m, 3H), 1.26 (d, J=6, 3H), 1.26–1.08 (m, 8H) and .92–.74 (m, 6H) |

EXAMPLE 12

N—(3-(S)—Methylheptanoyl)—D-gamma-glutamyl—L-alanyl—D-alanine ($R_1$ = (S) CH₃(CH₂)₃CH(CH₃)CH₂—;

$R_2$ = CH₃; $R_3$ = —NHCH(CH₃)CO₂H)

12A. N-t-butoxycarbonyl-L-alanyl-D-alanine benzyl ester

To a solution of 23.0 g. (0.121 m) of N-t-butoxycarbonyl-L-alanine, 42.6 g. (0.121 m) of D-alanine benzyl ester p-toluenesulfonic acid salt and 17 ml. (0.121 m) of triethylamine in 400 ml. of cold (0° C.) methylene chloride was added dropwise 25.0 g. (0.121 m) of dicyclohexylcarbodiimide in 100 ml. of methylene chloride. After stirring overnight at room temperature the solids were filtered and the filtrate concentrated to an oil. The residue was dissolved in 400 ml. of ethyl acetate which was washed with a 1% hydrochloric acid solution, a 10% potassium carbonate solution, water and a brine solution. The organic phase was separated, dried over magnesium sulfate and concentrated to an oil. The residue was triturated with diethyl ether and the resulting solids filtered under nitrogen, 16.0 g. An additional 12.7 g. of the desired product crystallized from the filtrate.

12B. L-alanyl-D-alanine benzyl ester hydrochloride

To a slurry of 28.7 g. of N-t-butoxycarbonyl-L-alanyl-D-alanine benzyl ester in 150 ml. of dioxane saturated with hydrogen chloride and the mixture stirred for 4 hours at room temperature. The solvent was removed in vacuo and the residue triturated with diethyl ether. The resulting solids were filtered, redissolved in methylene chloride and the solution concentrated to about 150 ml. Ether was added and the solids filtered under nitrogen, 22.0 g.

12C. N-t-butoxycarbonyl-D-gamma-glutamyl (alpha benzyl ester)-L-alanyl-D-alanine benzyl ester To a slurry of 5.0 g. (9.64 mm) N-t-butoxycarbonyl-D-gamma-glutamine alpha benzyl ester dicyclohexylamine and 2.76 g. (9.64 mm) of L-alanyl-D-alanine benzyl ester hydrochloride in 100 ml. of methylene chloride cooled to 0° C. was added 2.0 g. (9.64 mm) of dicyclohexylcarbodiimide in 20 ml. of the same solvent.

After stirring overnight at room temperature, the solids were filtered and the filtrate concentrated in vacuo. The residue was treated with 150 ml. of ethyl acetate, the solids filtered and the filtrate washed with 1% hydrochloric acid, a 10% potassium carbonate solution, water and a brine solution. The organic phase was dried over sodium sulfate and concentrated to give a white solid, which when triturated with ether and filtered gave 4.1 g. of the desired product.

12D. D-gamma-glutamyl (alpha benzyl ester)-L-alanyl-D-alanine benzyl ester hydrochloride To a slurry of 4.1 g. (7.21 mm) of N-t-butoxy-carbonyl-D-gamma-glutamyl (alpha benzyl ester)-L-alanyl-D-alanine benzyl ester in 50 ml. of dioxane was added 100 ml. of dioxane saturated with hydrogen chloride, and the reaction mixture stirred for 3 hours at room temperature. The solvent was removed under vacuum and the residue triturated with diethyl ether, 3.5 g.

12E. N-(3-(S)-methylheptanoyl)-D-gamma-glutamyl (alpha benzyl ester)-L-alanyl-D-alanine benzyl ester To 1.0 g. (1.98 mm) of D-gamma-glutamyl (alpha benzyl ester)-L-alanyl-D-alanine benzyl ester and .833 ml. (5.93 mm) of triethyl amine in 50 ml. of methylene chloride was added 390 mg. (2.37 mm) of 3-(S)-methylheptanoyl chloride and the reaction mixture stirred under nitrogen for 45 minutes. The reaction was poured into 150 ml. of ethyl acetate and the organic phase was washed with 10% hydrochloric acid, a 10% potassium carbonate solution, water and a brine solution. The organic phase was dried over sodium sulfate and concentrated to dryness. The residue was triturated with ether and filtered under nitrogen, 900 mg.

12F. N-(3-(S)-methylheptanoyl-D-gamma-glutamyl-L-alanyl-D-alanine

A mixture of 200 mg. of palladium hydroxide on carbon and 900 mg. of N-(3-(S)-methylheptanoyl)-D-gammaglutamyl (alpha benzyl ester)-L-alanyl-D-alanine benzyl ester in 50 ml. of methanol was shaken in a hydrogen atmosphere at 50 psi for one hour. The catalyst was filtered and the solvent removed in vacuo. Water was added to the residue and removed under reduced pressure to give 492 mg. of the product as a white solid, m.p. 165°–168° C.

The NMR spectrum (DMSO-d$_6$) showed absorption at 8.21–7.98 (m, 3H), 4.41–4.1 (m, 3H), 2.3–2.06 (m, 4H), 2.06–1.56 (m, 6H), 1.43–1.02 (m, 11H) and 1.02–0.73 (m, 6H) ppm.

EXAMPLE 13

N—(3-(S,R)—Ethylhexanoyl)—D-gamma-glutamyl
    (alpha n-butyl ester)—glycyl—D-alanine
(R$_1$ = CH$_3$(CH$_2$)$_2$CH(C$_2$H$_5$)CH$_2$—; R$_2$ = H;

D
R$_3$ = —NHCH(CH$_3$)CO$_2$H; R$_4$ = n-C$_4$H$_9$

13A. N-t-butoxycarbonyl-D-gamma-glutamine (alpha n-butyl ester)dicyclohexylamine salt A solution of 39.5 g. (0.172 m) of N-t-butoxycarbonyl-D-glutamic anhydride in 75 ml. of dry tetrahydrofuran was added dropwise over a two hour period to a solution of 47 ml. (0.516 m) and 34.3 ml. (0.172 m) of dicyclohexylamine in 300 ml. of ether at 0° C. The reaction was allowed to stir at 0° C. for 3 hours and was stored in a refrigerator overnight. The solids were filtered, slurried in ethanol and filtered, 43.3 g.

13B. D-gamma-glutamyl (alpha n-butyl ester)-glycyl-D-alanine benzyl ester hydrochloride The product of Example 13A (10 g., 0.021 m) and 6.7 g. (0.024 m) of glycyl-D-alanine benzyl ester hydrochloride were slurried in 200 ml. of methylene chloride under nitrogen and cooled to 0° C. Dicyclohexylcarbodiimide (4.25 g., 0.021 m) was added and the mixture allowed to warm to room temperature overnight. The urea byproduct was filtered and the solvent removed in vacuo. The residue was treated with ethyl acetate and filtered. The filtrate was washed successively with water, 2.5% hydrochloric acid, water, 10% potassium carbonate and brine. The organic phase was dried over magnesium sulfate, the solvent removed under vacuum and the residue dissolved in 300 ml. of dioxane saturated with hydrogen chloride. After stirring 4 hours at room temperature, the solvent was removed and the residue triturated in ethyl acetate-hexane (1:1) and filtered, 7.4 g.

13C. N-(3-(S,R)-ethylhexanoyl-D-glutamyl(alpha n-butyl ester)glycyl-D-alanine To the product of Example 13B (1.0 g., 2.35 mm) and 0.99 ml. (7.05 mm) of triethylamine in 50 ml. of methylene chloride was added 460 mg. (2.83 mm) of 3-(S,R) ethylhexanoyl chloride and the reaction stirred overnight under nitrogen. The solvent was removed in vacuo and the residue dissolved in ethyl acetate. The organic phase was successively washed with 10% hydrochloric acid, water 10% potassium carbonate and brine. The organic phase was separated, dried over magnesium sulfate and the solvent removed under vacuum. The residue was dissolved in 10 ml. of emthanol and shaken with 170 mg. of 10% palladium hydroxide in a hydrogen atmosphere at an initial pressure of 50 psi for 1.5 hours.

The spent catalyst was filtered and the solvent removed in vacuo, 100 mg.

NMR (DMSO-d$_6$) 8.18 (d, J=6, 1H), 8.10 (d, J=6, 1H), 8.02 (t, J=5, 1H), 4.28–4.10 (m, 2H), 4.00 (t, J=6, 2H), 3.78–3.56 (m, 2H), 2.18 (t, J=6, 2H), 2.02 (d, J=6, 2H), 2.00–1.60 (m, 3H), 1.58–1.42 (m, 2H), 1.28–1.08 (m, 8H), 1.24 (d, J=6, 3H), 0.92–0.76 (m, 9H).

EXAMPLE 14

Employing the general procedure of Example 13, and starting with the requisite reagents, the following compounds were prepared:

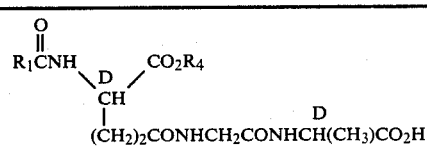

| R$_1$ | R$_4$ | NMR |
|---|---|---|
| 3-methylheptanoyl | methyl | NMR (DMSO—d$_6$): 8.23 (d, J=6, 1H), 8.15 (d, J=6, 1H), 8.09 (t, J=6, 1H), 4.28–4.14 (m, 2H); 3.72 (d, J=6, 2H), 3.61 (s, 3H), 2.23 (t, J=7, 2H), 2.16–1.70 (m, 6H), 1.34–1.04 (m, 8H), 1.25 (d, |

-continued

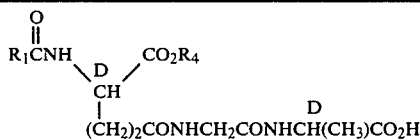

| $R_1$ | $R_4$ | NMR |
|---|---|---|
| 3-ethylheptanoyl | methyl | J=7, 3H), 0.92-0.76 (m, 6H). NMR (DMSO—$d_6$): 8.19 (d, J=6, 1H), 8.11 (d, J=6, 1H), 8.03 (t, J=6, 1H), 4.24-4.10 (m, 2H), 3.74-3.62 (m, 2H), 3.57 (s, 3H), 2.18 (t, J=9, 2H), 2.01 (d, J=6, 2H), 1.97-1.60 (m, 3H), 1.32-1.10 (m, 8H), 1.23 (d, J=7, 3H), 0.90-0.72 (m, 6H) |
| 3-methylheptanoyl | ethyl | NMR (DMSO—$d_6$): 8.24-8.02 (m, 3H), 4.26-3.96 (m, 2H), 4.04 (q, J=9, 2H), 3.76-3.56 (m, 2H), 2.17 (t, J=7, 2H), 2.12-1.63 (m, 6H); 1.74-0.94 (m, 6H), 1.23 (d, J=5, 3H), 1.13 (t, J=9, 3H), 0.88-0.72 (m, 6H) |
| 3-ethylheptanoyl | ethyl | NMR (DMSO—$d_6$): 8.16 (d, J=6, 1H), 8.09 (d, J=6, 1H), 8.02 (t, J=6, 1H), 4.22-4.08 (m, 2H), 4.02 (q, J=7, 2H), 3.74-3.54 (m, 2H), 2.16 (t, J=7, 2H), 2.00 (d, J=6, 2H), 1.96-1.58 (m, 3H), 1.30-1.08 (m, 8H), 1.21 (d, J=7, 3H), 1.13 (t, J=7, 3H), 0.88-0.70 (m, 6H) |
| 3-methylheptanoyl | iso-butyl | NMR (DMSO—$d_6$): 8.14 (d, J=6, 1H), 8.08-7.98 (m, 2H), 4.20-4.04 (m, 2H), 3.75 (d, J=6, 2H), 3.68-3.54 (m, 2H), 2.14 (t, J=6, 2H), 2.08-1.64 (m, 6H), 1.28-0.96 (m, 6H), 1.19 (d, J=7, 3H), 0.88-0.70 (m, 12H) |
| 3-ethylheptanoyl | iso-butyl | NMR (DMSO—$d_6$): 8.21 (d, J=6, 1H), 8.14-8.04 (m, 2H), 4.24-4.08 (m, 2H), 3.79 (d, J=6, 2H), 3.72-3.58 (m, 2H), 2.19 (t, J=7, 2H), 2.03 (d, J=6, 2H), 1.99-1.60 (m, 4H), 1.32-1.10 (m, 8H), 1.23 (d, J=6, 3H), 0.92-0.72 (m, 12H) |
| 3-ethylhexanoyl | iso-butyl | NMR (DMSO—$d_6$): 8.18 (d, J=6, 1H), 8.10-8.00 (m, 2H), 4.26-4.08 (m, 2H), 3.79 (d, J=6, 2H), 3.72-3.58 (m, 2H), 2.18 (t, J=6, 2H), 2.02 (d, J=6, 2H), 1.98-1.62 (m, 4H), 1.34-1.08 (m, 6H), 1.23 (d, J=7, 3H), 0.96-0.72 (m, 12H) |
| 3-ethylhexanoyl | methyl | NMR (DMSO—$d_6$): 8.21 (d, J=7, 1H), 8.10 (d, J=7, 1H), 8.05 (t, J=6, 1H), 4.26-4.10 (m, 2H), 3.76-3.60 (m, 2H), 3.59 (s, 3H), 2.18 (t, J=6, 2H), 2.02 (d, J=6, 2H), 2.00-1.60 (m, 3H), 1.32-1.08 (m, 7H), 0.90-0.72 (m, 6H). |
| 3-ethylhexanoyl | ethyl | NMR (DMSO—$d_6$): 8.22 (d, J=7, 1H), 8.18-8.06 (m, 2H), 4.26-4.10 (m, 2H), 4.06 (q, J=5, 2H), 3.78- |

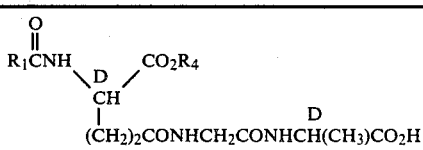

| $R_1$ | $R_4$ | NMR |
|---|---|---|
| | | 3.58 (m, 2H), 2.20 (t, J=6, 2H), 2.04 (d, J=6, 2H), 2.02-1.60 (m, 3H), 1.26-1.20 (m, 7H), 1.18 (t, J=5, 3H), 0.90-0.78 (m, 6H) |
| 3-methylheptanoyl | butyl | NMR (DMSO—$d_6$): 8.20 (d, J=7, 1H), 8.16-8.04 (m, 2H), 4.24-4.06 (m, 2H), 4.00 (t, J=6, 2H), 3.74-3.56 (m, 2H), 2.17 (t, J=6, 2H), 2.12-1.60 (m, 5H), 1.58-1.40 (m, 2H), 1.36-1.00 (m, 8H), 1.21 (d, J=6, 3H), 0.90-0.74 (m, 9H) |
| 3-ethylheptanoyl | butyl | NMR (DMSO—$d_6$): 8.16 (d, J=7, 1H), 8.11 (d, J=7, 1H), 8.03 (t, J=5, 1H), 4.26-4.09 (m, 2H), 3.99 (t, J=7, 2H), 3.79-3.58 (m, 2H), 2.17 (t, J=6, 2H), 2.01 (d, J=6, 2H), 2.00-1.60 (m, 3H), 1.58-1.42 (m, 2H), 1.36-1.08 (m, 10H), 1.24 (d, J=5, 3H), 0.92-0.72 (m, 9H) |

EXAMPLE 15

N—(3-(R,S)—Ethylhexanoyl)—D-gamma-glutamyl—glycyl—D-alanine ethyl ester ($R_1$ = $CH_3(CH_2)_2CH(C_2H_5)CH_2$—;

$$R_2 = H; R_3 = \overset{D}{-HNCH(CH_3)CO_2C_2H_5}; R_5 = H)$$

15A. D-gamma-glutamyl (alpha benzyl ester)glycyl-D-alanine ethyl ester hydrochloride To a slurry of 14.8 g. (0.0285 m) of N-t-butoxycarbonyl-D-gamma-glutamic acid alpha benzyl ester dicyclohexylamine salt acid 6 g. (0.0285 m) of glycyl-D-alanine ethyl ester hydrochloride in 200 ml. of methylene chloride was added 5.6 g. (0.0270 m.) of dicyclohexylcarbodiimide and the mixture stirred under a nitrogen atmosphere overnight. The urea is filtered and the solvent removed in vacuo. The residue was treated with 300 ml. of ethyl acetate, filtered and the filtrate washed successively with 2.5% hydrochloric acid, water, 10% potassium carbonate solution and brine. The organic phase was separated, dried over magnesium and concentrated under vacuum. The residual oil was dissolved in 450 ml. of dioxane saturated with hydrogen chloride. The solution was stirred for 2 hours and the solvent removed in vacuo. The residue was triturated with ether and filtered, 11.2 g.

15B. N(3-(R,S)-ethylhexanoyl)-D-gamma-glutamyl-glycyl-D-alanine ethyl ester

To the product of Example 15A (1.0 g., 2.33 mm.) and 0.98 ml. (6.98 mm.) of triethylamine in 30 ml. of methylene chloride, under a nitrogen atmosphere, was added 378 mg. (2.33 mm.) of 3-(R,S)-ethylhexanoyl chloride. After stirring at room temperature for 1.5 hours the mixture was poured into 100 ml. of ethyl acetate and the organic phase was washed successively with 10% potassium carbonate solution and brine. The organic phase was separated, dried over magnesium sulfate and concentrated in vacuo. The white solid residue was dissolved in 30 ml. of methanol palladium hydroxide in a hydrogen atmosphere at an initial pressure of 50 psi. After 2 hours the catalyst was filtered, the filtrate concentrated to dryness and the residue triturated with ether and filtered, 275 mg.

NMR (DMSO-$d_6$) 8.26 (d, J=9, 1H), 8.14–8.02 (m, 2H), 4.31–4.00 (m, 2H), 4.06 (q, J=10, 2H), 3.78–3.60 (m, 2H), 2.17 (t, J=8, 2H), 2.08–1.65 (m, 1H), 2.03 (d, J=8, 2H), 1.82–1.53 (m, 3H), 1.40–0.96 (m, 5H), 1.23 (d, J=6, 3H), 1.14 (t, J=10, 3H), 0.90–0.64 (m, 6H).

EXAMPLE 16

Starting with the appropriate reagents and employing the procedure of Example 15A–15B, the following compounds were prepared:

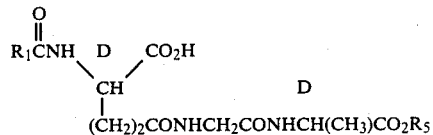

| $R_1$ | $R_5$ | NMR |
|---|---|---|
| 3-methylheptanoyl | iso-butyl | NMR (DMSO-$d_6$): 8.24 (d, J=6, 1H), 8.10–8.00 (m, 2H), 4.30–4.18 (m, 1H), 4.18–4.08 (m, 1H), 3.86–3.72 (m, 2H), 3.72–3.58 (m, 2H), 2.16 (t, J=6, 2H), 2.12–1.64 (m, 6H), 1.52–1.00 (m, 6H), 1.27 (d, J=7, 3H), 0.90–0.76 (m, 12H) |
| 3-ethylhexanoyl | iso-butyl | NMR (DMSO-$d_6$): 8.23 (d, J=6, 1H), 8.08–7.99 (m, 2H), 4.29–4.17 (m, 1H), 4.17–4.07 (m, 1H), 3.83–3.71 (m, 2H), 3.71–3.58 (m, 2H), 2.15 (t, J=7, 2H), 2.04–1.60 (m, 4H), 2.00 (d, J=6, 2H), 1.31–1.09 (m, 6H), 1.25 (d, J=6, 3H), 0.90–0.72 (m, 12H) |
| 3-ethylheptanoyl | iso-butyl | NMR (DMSO-$d_6$): 8.23 (d, J=6, 1H), 8.08–7.98 (m, 2H), 4.29–4.18 (m, 1H), 4.18–4.07 (m, 1H), 3.86–3.72 (m, 2H), 3.70–3.57 (m, 2H), 2.15 (t, J=7, 2H), 2.04–1.59 (m, 4H), 2.00 (d, J=6, 2H), 1.30–1.11 (m, 8H), 1.25 (d, J=6, 3H), 0.89–0.70 (m, 12H) |
| 3-methylheptanoyl | methyl-cyclohexyl | NMR (DMSO-$d_6$): 8.25 (d, J=6, 1H), 8.13–8.00 (m, 2H), 4.32–4.20 (m, 1H), 4.20–4.08 (m, 1H), 3.91–3.76 (m, 2H), 3.76–3.59 (m, 2H), 2.18 (t, J=6, 2H), 2.13–1.48 (m, 8H), 1.36–1.01 (m, 12H), 1.27 (d, J=6, 3H), 1.02–0.76 (m, 8H) |
| 3-ethylhexanoyl | methyl-cyclohexyl | NMR (DMSO-$d_6$): 8.25 (d, J=6, 1H), 8.13–8.00 (m, 2H), 4.32–4.20 (m, 1H), 4.20–4.08 (m, 1H), 3.92–3.74 (m, 2H), 3.74–3.59 (m, 2H), 2.18 (t, J=6, 2H), 2.09–1.86 (m, 1H), 2.03 (d, J=6, 2H), 1.82–1.43 (m, 8H), 1.36–1.01 (m, 9H), 1.27 (d, J=6, 3H), 1.01–0.70 (m, 8H) |
| 3-ethylheptanoyl | methyl-cyclohexyl | NMR (DMSO-$d_6$): 8.26 (d, J=6, 1H), 8.12–8.02 (m, 2H), 4.31–4.19 (m, 1H), 4.19–4.08 (m, 1H), 3.93–3.72 (m, 2H), 3.72–3.58 (m, 2H), 2.18 (t, J=6, 2H), 2.08–1.86 (m, 1H), 2.03 (d, J=6, 2H), 1.82–1.48 (m, 8H), 1.34–1.02 (m, 11H), 1.27 (d, J=6, 3H), 1.00–0.74 (m, 8H) |
| 3-methylheptanoyl | ethyl | NMR (DMSO-$d_6$): 8.25 (d, J=6, 1H), 8.12–8.00 (m, 2H), 4.28–3.96 (m, 2H), 4.03 (q, J=7, 2H), 3.74–3.56 (m, 2H), 2.16 (t, J=9, 2H), 2.11–1.62 (m, 6H), 1.32–0.98 (m, 6H), 1.24 (d, J=7, 3H), 1.14 (t, J=7, 3H), 0.88–0.76 (m, 6H) |
| 3-ethylheptanoyl | ethyl | NMR (DMSO-$d_6$): 8.28 (d, J=6, 1H), 8.16–8.04 (m, 2H), 4.32–4.04 (m, 2H), 4.10 (q, J=6, 2H), 3.78–3.64 (m, 2H), 2.22 (t, J=6, 2H), 2.11–1.92 (m, 1H), 2.07 (d, J=6, 2H), 1.86–1.64 (m, 2H), 1.40–1.14 (m, 8H), 1.30 (d, J=6, 3H), 1.21 (t, (J=6, 3H), 0.94–0.76 (m, 6H). |
| 3-ethylheptanoyl | butyl | NMR (DMSO-$d_6$): 8.27 (d, J=8, 1H), 8.14–8.02 (m, 2H), 4.32–4.10 (m, 2H), 4.10–3.94 (m, 2H), 3.78–3.60 (m, 2H), 2.18 (t, J=6, 2H), 2.04 (d, J=6, 2H), 2.04–1.62 (m, 3H), 1.60–1.46 (m, 2H), 1.38–1.10 (m, 12H), 1.27 (d, J=6, 3H), 0.90–0.75 (m, 9H) |
| 3-S—methylheptanoyl | butyl | NMR (DMSO-$d_6$): 8.30 (d, J=8, 1H), 8.15–8.04 (m, 2H), 4.45–4.12 (m, 2H), 4.12–3.98 (m, 2H), 3.78–3.65 (m, 2H), 2.22 (t, J=7, 2H), 2.18–1.69 (m, 7H), 1.61–1.48 (m, 2H), 1.40–1.11 (m, 11H), 0.97–0.80 (m, 9H) |
| 3-S—ethylheptanoyl | butyl | NMR (DMSO-$d_6$): 8.22 (d, J=7, 1H), 8.12–8.0 (m, 2H), 4.4–4.16 (m, 2H), 4.08–3.95 (m, 2H), 3.75–3.62 (m, 2H), 2.18 (t, J=6, 2H), 2.02 (d, J=6, 2H), 2.04–1.62 (m, 3H), 1.60–1.46 (m, 2H), 1.38–1.1 (m, 15H), and .9–.75 (m, 9H) |

-continued

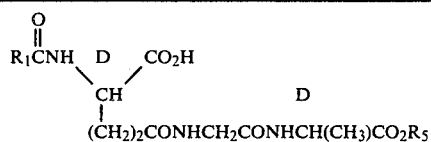

| $R_1$ | $R_5$ | NMR |
|---|---|---|
| 3-ethylhexanoyl | butyl | NMR (DMSO-$d_6$): 8.28 (d, J=8, 1H), 8.14–8.04 (m, 2H), 4.34–4.10 (m, 2H), 4.10–3.95 (m, 2H), 3.75–3.62 (m, 2H), 2.19 (t, J=6, 2H), 2.04 (d, J=6, 2H), 2.04–1.60 (m, 3H), 1.60–1.45 (m, 2H), 1.40–1.10 (m, 13H), 0.90–0.76 (m, 9H) |

EXAMPLE 17

The procedure of Example 15 is again repeated, starting with the appropriate reagents, with the exception that the hydrogenation is not carried out, to give the following compounds:

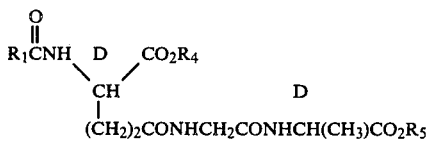

| $R_1$ | $R_4$ | $R_5$ | NMR |
|---|---|---|---|
| 3-ethyl-hexanoyl | butyl | butyl | NMR (DMSO-$d_6$): 8.27 (d, J=7, 1H), 8.20 (d, J=7, 1H), 8.07 (t, J=7, 1H), 4.37–4.13 (m, 2H), 4.02 (t, J=6, 4H), 3.80–3.62 (m, 2H), 2.20 (t, J=6, 2H), 2.05 (d, J=6, 2H), 2.02–1.64 (m, 3H), 1.60–1.47 (m, 4H), 1.40–1.13 (m, 13H), 0.95–0.77 (m, 12H) |
| 3-ethyl-heptanoyl | butyl | butyl | NMR (DMSO-$d_6$): 8.27 (d, J=7, 1H), 8.20 (d, J=7, 1H), 8.06 (t, J=6, 1H), 4.36–4.13 (m, 2H), 4.02 (t, J=6, 4H), 3.80–3.60 (m, 2H), 2.20 (t, J=6, 2H), 2.04 (d, J=6, 2H), 2.00–1.60 (m, 3H), 1.60–1.49 (m, 4H), 1.40–1.10 (m, 15H), 0.95–0.72 (m, 12H) |
| 3-methyl-heptanoyl | butyl | butyl | NMR (DMSO-$d_6$): 8.26 (d, J=7, 1H), 8.19 (d, J=7, 1H), 8.07 (t, J=6, 1H), 4.32–4.11 (m, 2H), 4.02 (t, J=5, 4H), 3.79–3.59 (m, 2H), 2.20 (t, J=6, 2H), 2.14–1.68 (m, 5H), 1.61–1.46 (m, 4H), 1.40–1.06 (m, 13H), 0.95–0.81 (m, 12H) |
| 3-S—methyl-heptanoyl | benzyl | benzyl | NMR (DMSO-$d_6$): 8.33 (d, J=7, 1H), 8.24 (d, J=7, 1H), 8.08 (t, J=5, 1H), 7.33 (s, 10H), 5.08 (s, 4H), 4.40–4.22 (m, 2H), 3.80–3.60 (m, 2H), 2.21 (t, J=5, 2H), 2.14–1.64 (m, 5H), 1.26 (d, J=7, 3H), 1.22–0.98 (m, 6H), 0.88–0.73 (m, 6H) |

EXAMPLE 18

Crystalline N-(3-(S)-methylheptanoyl)-D-gamma-glutamyl-glycyl-D-alanine

N-(3-(S)-Methylheptanoyl)-D-gamma-glutamyl (alpha benzyl ester)-glycyl-D-alanine benzyl ester (30.8 g.) was slurried in 300 ml. absolute ethanol in a 2 liter autoclave. 5% Pd/C, 1.54 g., 50% water wet) was added and the mixture hydrogenated at 4× atmospheric pressure for 1 hour, by which time uptake of hydrogen was complete. The catalyst was recovered by filtration, first over paper, then over 0.45 micro nylon milipore, employing 100–150 ml. ethanol for transfer and wash. The combined filtrate and wash liquors were stripped to a damp, white solid, which was dissolved in a 150 ml. of a hot, 1:10 mixture of absolute ethanol and acetonitrile, clarified by hot filtration, boiled down to 35 ml., slowly cooled to room temperature, granulated and filtered to yield crystalline, dense, non-electrostatic title product, 20.1 g. (94%) characterized by its ir (nujol mull) which includes major, well-resolved, sharp peaks at 3340, 3300, 2900, 2836, 1725, 1650, 1628, 1580, 1532, 1455, 1410, 1370, 1280, 1240, 1216 and 1175 cm$^{-1}$.

This crystalline product (9.4 g) was further purified by dissolving in 1000 ml. of acetone at reflux for 1 hour. The solution was cooled to room temperature and seeded with a trace of the above crystals. After stirring for 6 hours, title product was recovered by filtration with minimal acetone wash, and dried in vacuo at 35° C., 7.25 g., having identical ir characteristics.

EXAMPLE 19

N-(3-(R)-Methyl-4-heptenoyl)-D-gamma-glutamyl (alpha benzyl ester)-glycyl-D-alanine benzyl ester Following the procedure of Example 10D, 2.77 g. (5 mm) of D-gamma-glutamyl (alpha benzyl ester)-glycyl-D-alanine benzyl ester hydrochloride and the acid chloride prepared from 747 mg. (5 mm) of 3-(R)-methyl-4-heptenoic acid gave the titled compound.

EXAMPLE 20

N-(3-(S)-Methyl-4-heptanoyl)-D-gamma-glutamyl-glycyl-D-alanine

A mixture of 500 mg. of the product from Example 19 and 26 mg. of 5% palladium-on-charcoal (50% water wet) in 125 ml. of ethanol was shaken in a hydrogen atmosphere at an initial pressure of 4× atmospheric pressure for 2.5 hours. The catalyst was filtered and the solvent removed in vacuo. The product was purified by the procedure of Example 18, and was identical in all respects to the product of that example.

PREPARATION A

Cyclohexylacetyl chloride

A1. ethyl cyclohexylacetate

To 4.9 g. of 60% sodium hydride in oil was added sufficient hexane to dissolve the oil. To the oil free sodium hydride under nitrogen was added 100 ml. of dry tetrahydrofuran followed by a solution of 22.2 ml. of triethyl phosphonoacetate in 80 ml. of dry tetrahydrofuran. After stirring at room temperature for one hour 10.5 ml. of cyclohexanone was added in 40 ml. of tetrahydrofuran and the reaction mixture stirred at room temperature overnight. The reaction was poured into water and extracted with diethyl ether. The organic phase was washed with 1N sodium hydroxide solution, water and brine. The organic phase was separated, dried over magnesium sulfate and concentrated under reduced pressure.

The residue was dissolved in 250 ml. of methanol, treated with 1.5 g. of 10% palladium hydroxide on carbon and the mixture shaken in a hydrogen atmosphere at 50 psi for 4 hours. The catalyst was filtered and the filtrate concentrated in vacuo. The residue was distilled at 45°–50° C./0.4 torr to give 15.4 g. (90% yield) of the desired intermediate.

A2 cyclohexylacetyl chloride

To 100 ml. of methanol containing 15.4 g. of ethyl cyclohexylacetate was added 15.2 g. of potassium hydroxide and the solution refluxed for 3 hours. The methanol was removed in vacuo and the residue treated with water. The solution was extracted with diethyl ether and then acidified with 10% hydrochloric acid. The acidified solution was extracted with fresh ether and the organic phase separated and washed with water and a brine solution. Removal of the solvent after drying gave a liquid residue.

The residue was dissolved in 60 ml. of methylene chloride was treated with 18 ml. of oxalyl chloride. After stirring at room temperature for 4 hours the reaction mixture was concentrated under vacuum and the residue distilled, 45°/50° C./0.4 torr, 12.5 g. (86% yield).

PREPARATION B

Following the general procedure of Preparation A and starting with triethyl phosphonoacetal and the appropriate aldehyde or ketone the following acid chlorides were prepared:

| $R_1$COCl $R_1$ | B.P. °C./torr |
|---|---|
| $(CH_3CH_2CH_2)_2CHCH_2-$ | 50–55/0.4 |
| $(CH_3CH_2)_2CHCH_2-$ | 22–25/0.5 |
| $CH_3(CH_2)_3\overset{\underset{\mid}{CH_3}}{C}HCH_2-$ (R,S) | 23–30/0.5 |
| $CH_3(CH_2)_2\overset{\underset{\mid}{CH_3}}{C}HCH_2-$ (R,S) | 22–25/0.5 |
| $(CH_3)_2CH(CH_2)_3-$ | 24–31/0.7 |
| $CH_3(CH_2)_3\overset{\underset{\mid}{CH_3CH_2}}{C}HCH_2$ | 34–37/0.5 |
| $CH_3(CH_2)_4\overset{\underset{\mid}{CH_3}}{C}HCH_2$ (R,S) | 45–47/0.6 |
| cyclopentyl-$CH_2-$ | 25–30/0.5 |
| $(CH_3CH_2)_2CH(CH_2)_2-$ | 32–36/0.4 |

-continued

| $R_1$COCl $R_1$ | B.P. °C./torr |
|---|---|
| $CH_3(CH_2)_2\overset{\underset{\mid}{CH_3}}{C}H(CH_2)_2-$ (R,S) | 30–38/.06 |
| $CH_3(CH_2)_4\overset{\underset{\mid}{CH_3CH_2}}{C}HCH_2$ (R,S) | 63–65/.95 |
| $CH_3(CH_2)_5\overset{\underset{\mid}{CH_3}}{C}HCH_2-$ (R,S) | 89–92/5 |
| $(CH_3)_2CH(CH_2)_2\overset{\underset{\mid}{CH_3}}{C}HCH_2$ (R,S) | 46–50/0.5 |
| $(CH_3)_2CHCH_2\overset{\underset{\mid}{CH_3}}{C}HCH_2-$ (R,S) | 30–34/0.5 |
| $CH_3(CH_2)_2\overset{\underset{\mid}{CH_3CH_2}}{C}HCH_2-$ (R,S) | 31–35/0.7 |

PREPARATION C

6-Methylheptanoyl Chloride

C1. 3-hydroxy-4-methyl-1-pentene

To 90 ml. of 1.0M vinyl magnesium bromide in tetrahydrofuran cooled to 5° C. was added dropwise 6.3 ml. of isobutyraldehyde in 30 ml. of tetrahydrofuran and the mixture then allowed to warm to room temperature. After 2 hours the reaction was added to a saturated ammonium chloride solution and extracted with ether. The ether extracts were combined, washed with a saturated ammonium chloride solution, a saturated sodium bicarbonate solution and a brine solution, and dried over magnesium sulfate. The solvent was removed in vacuo to give 6.0 g. of the desired product.

C2. 6-methyl-4-heptanoic acid ethyl ester

A mixture of 18.2 g. of 3-hydroxy-4-methyl-1-pentene, 200 ml. of triethyl orthoformate and 500 ml. of p-toluenesulfonic acid was treated with 400 ml. of toluene and heated to reflux over 4A molecular sieves for 24 hours. The solvent was removed in vacuo and the residue distilled. The fraction distilling at 45°–64° C./0.5 torr gave 7.5 g. of the desired product.

C3. 6-methylheptanoic acid ethyl ester

To 7.5 g. of 6-methyl-4-heptanoic acid ethyl ester in 75 ml. of methanol was added 700 mg. of 10% palladium hydroxide on carbon and the mixture shaken in a hydrogen atmosphere at 50 psi for 1.5 hours. The catalyst was filtered and the solvent removed under vacuum to give 5.7 g. of the desired product.

C4. 6-methylheptanoyl chloride

Following the procedure of Preparation A2, 5.7 g. of 6-methylheptanoic acid ethyl ester gave 2.0 g. of the desired product, b.p. 30°–34° C./0.5 torr.

PREPARATION D

2-Methylheptanoyl chloride

D1. 2-methylheptanoic acid

To a cold (0° C.) solution of 100 ml. of dry tetrahydrofuran containing 11.8 ml. of dry diisopropylamine and 55 ml. of 1.6M n-butyl lithium was added 5.4 ml. of n-heptanoic acid and the mixture allow to stir at room temperature for one hour. The resulting solution was cooled to 0° C. and 7.2 ml. of methyl iodide was added. The reaction was stirred at room temperature under nitrogen for 1.5 hours, and was then poured into 10% hydrochloric acid and extracted with diethyl ether (3×100 ml.). The extracts were combined, washed with 10% hydrochloric acid, water, 20% sodium bisulfite and a brine solution and dried over magnesium sulfate. The solvent was removed in vacuo and the residue, 5.61 g., dissolved in methanol containing 5.1 g. of potassium hydroxide. After stirring overnight the mehtanol was removed and the residue dissolved in 150 ml. of water. The aqueous layer was washed with ether (2×100 ml.) and acidified with 10% hydrochloric acid. The product was extracted with ether, washed with a 20% sodium bisulfite solution and brine and dried over magnesium sulfate. Removal of the ether gave 5.0 g. of the product as a yellow liquid.

D2. 2-methylheptanoyl chloride

Employing 5 g. of 2-methylheptanoic acid and 7.6 ml. of oxalyl chloride and using the procedure of Preparation A2, 3.3 g. of the desired product was obtained, b.p. 32°-34 ° C./0.6 torr.

PREPARATION E

3-(S)-Methylheptanoyl chloride

E1. 3-(R)-methylglutaric acid mono methyl ester

To a 5 l. four necked flask fitted with a stirred and pH electrode was added 2.5 l. of 0.1M potassium acid phosphate buffer pH 7.0 followed by 150 mg. of pig liver esterase and 150 g. of dimethyl 3-methylglutarate. The pH of the mixture was maintained at about 6.85 by periodic addition of a 10% potassium carbonate solution. After 2.5 hours the reaction was acidified with 10% hydrochloric acid to pH 2.0 and the product extracted with diethyl ether. The extracts were combined, dried over magnesium sulfate and concentrated in vacuo to give 114 g. of the desired product, [alpha]$_D$=−1.48 (CH$_3$OH C=0.086 g/ml).

E2. methyl 3-(R)-methyl-5-hydroxypentanoate

To 114 g. of 3-(R)-methylglutaric acid mono methyl ester in 715 ml. of dry tetrahydrofuran cooled to 0° C. was added slowly 391 ml. of 2M solution of borane dimethylsulfide in tetrahydrofuran. After the addition was complete the reaction mixture was stirred overnight at room temperature. The reaction was cooled and 50 ml. of water slowly added. The reaction was extracted (3×100 ml.) with ether and the extracts combined, washed with water, a saturated sodium bicarbonate solution and a brine solution, and dried over magnesium sulfate. Removal of the solvent gave 37 g. of the desired product.

E3. methyl 3-(R)-methyl-5-(t-butyldimethylsilyloxy)pentanoate

To a solution of 37 g. (0.253 m) of methyl 3-(R)-methyl-5-hydroxypentanoate and 37 g. (0.543 m) of imidazole in 500 ml. of dimethylformamide was added 37 g. (0.249 m) of t-butyldimethylsilyl chloride and the reaction stirred at room temperature for 2 hours. The reaction mixture was poured into water and extracted (4×100 ml.) with ether. The combined extracts were washed with 10% hydrochloric acid, a saturated sodium bicarbonate solution, water and a brine solution, and dried over magnesium sulfate. Removal of the solvent gave 121.88 g. of crude product which, on distillation, gave 107.12 g. of pure product, b.p. 80°-81° C./0.4 torr.

E4. 3-(S)-methyl-5-(t-butyldimethylsilyloxy)-1-pentanol

To 8.5 g. (0.224 m) of lithium aluminum hydride in 250 ml. of diethyl ether under nitrogen was added 53.5 g. (0.206 m) of methyl 3-(R)-methyl-5-(t-butyldimethylsilyloxy)pentanoate in 125 ml. of ether. The reaction was stirred for one hour at 0° C. and was then treated dropwise with 8.4 g. of water, 8.4 ml. of a 15% sodium hydroxide solution and 25.2 ml. of water. The solids were filtered and the organic phase separated and washed with water, 2.5% hydrochloric acid and a brine solution. The organic phase was dried over magnesium sulfate and concentrated in vacuo to give 46 g. of product.

E5. 3-(R)-methyl-5-(t-butyldimethylsilyloxy)-1-pentanal

To 56.3 g. of oxalyl chloride in 300 ml. of dry methylene chloride cooled to −60° C. and under a nitrogen atmosphere was added dropwise 74.81 g. of dimethylsulfoxide in 100 ml. of dry methylene chloride. After 15 minutes 92.0 g. of 3-(S)-methyl-5-(t-butyldimethylsilyloxy)-1-pentanol in 250 ml. of the same solvent was added dropwise. After 30 minutes 206.1 g. of triethylamine was added to −60° C. followed by the removal of the cooling bath. The reaction was stirred at room temperature for 1.5 hours, and was then poured into water and extracted with methylene chloride. The extracts were washed with 2.5% hydrochloric, a saturated sodium bicarbonate solution, water and a brine solution, and then dried over magnesium sulfate. The solvent was removed and the residue dissolved in ether and rewashed and dried as before. Removal of the ether gave 90.9 g. of the desired product.

E6. 5-(S)-methyl-7-(t-butyldimethylsilyloxy)-2-heptene

To a slurry of 80 g. (0.2155 m) of triphenyl-ethyl phosphonium bromide in 800 ml. of dry tetrahydrofuran cooled to 0° C. was added 165.7 ml. of 1.3M solution of n-butyl lithium (0.2155 m) in the same solvent. After 2 hours, 45 g. (0.196 m) 3-(R)-methyl-5-(t-butyldimethylsilyloxy)-1-pentanal in 200 ml. of dry tetrahydrofuran was added dropwise to the reaction mixture. The reaction was allowed to stir 2 hours at room temperature and was then poured into water and extracted with ether. The combined extracts were washed with water and a brine solution and dried over magnesium sulfate. Removal of the solvent in vacuo gave a yellow oil which, on distillation gave 37.4 g. of product, b.p. 74°-79° C./0.2-0.1 torr.

E7. 3-(S)-methyl-1-heptanol

To a solution of 74.8 g. of 5-(S)-methyl-7-(t-butyldimethylsilyloxy)-2-heptene in 500 ml. of methanol was added 7.5 g. of 10% palladium hydroxide on carbon and the mixture shaken in a hydrogen atmosphere for 1.5 hours at 50 psi. The catalyst was filtered and the solvent removed under vacuum, 30 g.

E8. 3-(S)-methylheptanoic acid

To 10 g. of 3-(S)-methyl-1-heptanol in 175 ml. of acetone was added over 45 minutes 90 ml. of Jones reagent dropwise at 15°–20° C. After 15 minutes, 15 ml. of isopropanol was added and stirring continued for 30 minutes. The reaction was poured into water and the product extracted with ether. The extracts were combined, washed with water, a sodium bisulfite solution and a brine solution and dried over magnesium sulfate. Removal of the solvent gave 10 g. of the product as a liquid, b.p. 84°–88° C./0.4 torr, [alpha]$_D$=−4.46 ($CH_3OH$ C=0.105 g/ml.).

E9. 3-(S)-methylheptanoyl chloride

Following the procedure of Preparation A2, 5.0 g. of 3-(S)-methylheptanoic acid and 7.5 ml. of oxalyl chloride gave 2.9 g. of the desired acid chloride, b.p. 29°–32° C./0.25 torr.

I claim:

1. A compound of the formula

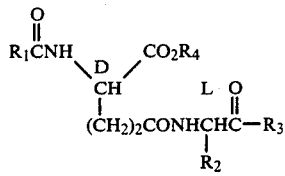

and pharmaceutically acceptable base salt thereof, wherein $R_1$ is selected from the group consisting of cycloalkyl having four to seven carbon atoms, alkyl having two to ten carbon atoms and cycloalkylmethyl having from six to eight carbon atoms; $R_2$ is hydrogen; $R_3$ is a D-amino acid residue of the formula

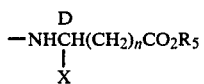

wherein X is selected from the group consisting of hydrogen, alkyl having one to two carbon atoms and hydroxymethyl, and n is an integer of 0 to 4; and $R_4$ and $R_5$ are each selected from the group consisting of hydrogen, alkyl having one to six carbon atoms, cycloalkylmethyl having six to eight carbon atoms and benzyl.

2. A compound of claim 1, wherein $R_1$ is alkyl having five to eight carbon atoms, $R_3$ is an amino acid residue of the formula $$-\underset{X}{NHCH}(CH_2)_nCO_2R_5$$

wherein X is selected from the group consisting of hydrogen and alkyl having one to two carbon atoms, n is an integer of 0 to 4 and $R_5$ is selected from the group consisting of hydrogen, alkyl having one to six carbon atoms, cycloalkylmethyl having six to eight carbon atoms and benzyl, and $R_4$ is hydrogen.

3. A compound of claim 2, wherein n is 0 and $R_5$ is selected from the group consisting of hydrogen, alkyl having one to six carbon atoms and cyclohexylmethyl.

4. The compound of claim 3, wherein $R_1$ is (S,R) 2-ethyl-1-butyl and X is methyl and $R_5$ is hydrogen.

5. The compound of claim 3, wherein $R_1$ is (S,R) 3-heptyl and X is methyl and $R_5$ is hydrogen.

6. The compound of claim 3, wherein $R_1$ is (S,R) 2-heptyl and X is methyl and $R_5$ is hydrogen.

7. The compound of claim 3, wherein $R_1$ is (S,R) 2-ethyl-1-pentyl, X is methyl and $R_5$ is hydrogen.

8. The compound of claim 3, wherein $R_1$ is (S,R) 2-ethyl-1-pentyl, X is methyl and $R_5$ is n-butyl.

9. The compound of claim 3, wherein $R_1$ is (S,R) 2-ethyl-1-pentyl, X is methyl and $R_5$ is i-butyl.

10. The compound of claim 3, wherein $R_1$ is (S,R) 2-ethyl-1-pentyl, X is methyl and $R_5$ is cyclohexylmethyl.

11. The compound of claim 3, wherein $R_1$ is (S) 2-methyl-1-hexyl, X is methyl and $R_5$ is hydrogen.

12. The compound of claim 3, wherein $R_1$ is (S) 2-methyl-1-hexyl, X is methyl and $R_5$ is n-butyl.

13. The compound of claim 3, wherein $R_1$ is (S,R) 2-ethyl-1-hexyl, X is methyl and $R_5$ is hydrogen.

14. The compound of claim 3, wherein $R_1$ is (S,R) 2-ethyl-1-hexyl, X is methyl and $R_5$ is n-butyl.

15. The compound of claim 3, wherein $R_1$ is (S,R) 2-ethyl-1-hexyl, X is methyl and $R_5$ is i-butyl.

16. The compound of claim 3, wherein $R_1$ is (S,R) 2-ethyl-1-hexyl, X is methyl and $R_5$ is cyclohexylmethyl.

17. The compound of claim 3, wherein $R_1$ is (S) 2-ethyl-1-hexyl, X is methyl and $R_5$ is hydrogen.

18. The compound of claim 3, wherein $R_1$ is (S) 2-ethyl-1-hexyl, X is methyl and $R_5$ is n-butyl.

19. The compound of claim 3, wherein $R_1$ is (S) 2-ethyl-1-hexyl, X is methyl and $R_5$ is cyclohexylmethyl.

20. The compound of claim 3, wherein $R_1$ is (S,R) 2-methyl-1-hexyl, X is methyl and $R_5$ is hydrogen.

21. The compound of claim 3, wherein $R_1$ is (S,R) 2-methyl-1-hexyl, X is methyl and $R_5$ n-butyl.

22. The compound of claim 3, wherein $R_1$ is (S,R) 2-methyl-1-hexyl, X is methyl and $R_5$ is i-butyl.

23. The compound of claim 3, wherein $R_1$ is (S,R) 2-methyl-1-hexyl, X is methyl and $R_5$ is cyclohexylmethyl.

24. The compound of claim 3, wherein $R_1$ is (S,R) 2-methyl-1-pentyl, X is methyl and $R_5$ is hydrogen.

25. The compound of claim 3, wherein $R_1$ (S,R) 1-hexyl, X is methyl and $R_5$ is hydrogen.

26. The compound of claim 2, wherein $R_1$ is 1-hexyl, X is hydrogen, n is 3 and $R_5$ is hydrogen.

27. A compound of claim 1, wherein $R_1$ is cycloalkyl having four to seven carbon atoms, $R_3$ is an amino acid residue of the formula

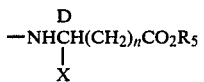

wherein n is 0 and X is alkyl having one to two carbon atoms and $R_4$ and $R_5$ are each hydrogen.

28. The compound of claim 27, wherein $R_1$ is cyclohexyl and X is methyl.

29. A compound of claim 1, wherein $R_1$ is alkyl having five to eight carbon atoms, $R_3$ is an amino acid residue of the formula

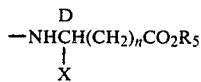

wherein X is selected from the group consisting of hydrogen and alkyl having one to two carbon atoms, n is an integer of 0 to 4 and $R_5$ is hydrogen, and $R_4$ is selected from the group consisting of alkyl having one to six carbon atoms, cycloalkylmethyl having six to eight carbon atoms and benzyl.

30. A pharmaceutical composition in unit dosage form comprising a pharmaceutically acceptable carrier and an antiinfective or immunostimulant effective amount of a compound according to claim 1.

31. A method for treating an infection in a human suffering therefrom which comprises administering to said human an antiinfective amount of a compound according to claim 1.

* * * * *